US011253142B2

(12) United States Patent
Morishima

(10) Patent No.: US 11,253,142 B2
(45) Date of Patent: Feb. 22, 2022

(54) VARIABLE-STIFFNESS ACTUATOR SYSTEM

(71) Applicant: OLYMPUS CORPORATION, Tokyo (JP)

(72) Inventor: Tetsuya Morishima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 596 days.

(21) Appl. No.: 16/163,697

(22) Filed: Oct. 18, 2018

(65) Prior Publication Data
US 2019/0046008 A1 Feb. 14, 2019

Related U.S. Application Data

(63) Continuation of application No. PCT/JP2016/062241, filed on Apr. 18, 2016.

(51) Int. Cl.
*A61B 1/005* (2006.01)
*A61B 1/00* (2006.01)
*A61M 25/01* (2006.01)

(52) U.S. Cl.
CPC .............. *A61B 1/0058* (2013.01); *A61B 1/00* (2013.01); *A61B 1/00078* (2013.01);
(Continued)

(58) Field of Classification Search
CPC ............ A61B 1/00087; A61B 1/00119; A61B 1/00131; A61B 1/00147; A61B 1/0058; A61B 1/015; A61B 1/126
See application file for complete search history.

(56) References Cited

U.S. PATENT DOCUMENTS 4,281,646 A * 8/1981 Kinoshita .......... A61B 1/00068
600/157
4,509,507 A * 4/1985 Yabe .................. A61B 1/00068
600/158
(Continued)

FOREIGN PATENT DOCUMENTS

JP S58-101601 U 7/1983
JP S58-101602 U 7/1983
(Continued)

OTHER PUBLICATIONS

English translation of International Preliminary Report on Patentability dated Nov. 1, 2018 together with the Written Opinion received in related International Application No. PCT/JP2016/062241.
(Continued)

*Primary Examiner* — Aaron B Fairchild
(74) *Attorney, Agent, or Firm* — Scully, Scott, Murphy & Presser, P.C.

(57) ABSTRACT

A variable-stiffness actuator system includes a shape-memory member in which a stiffness increases by being heated and decreases by radiating heat, a heating member configured to generate heat, a channel arranged along the longitudinal axis of the shape-memory member, a transfer section configured to selectively supply and stop first and second heat transmission fluids into the channel, and a controller configured to control the transfer section. The controller causes the transfer section to supply the first heat transmission fluid and then supply the second heat transmission fluid into the channel, and further to stop the supply of the second heat transmission fluid so that retention of the first and second heat transmission fluids simultaneously occurs in the channel.

21 Claims, 14 Drawing Sheets

(52) U.S. Cl.
CPC ...... *A61B 1/00119* (2013.01); *A61B 1/00131* (2013.01); *A61B 1/00147* (2013.01); *A61B 2560/04* (2013.01); *A61M 25/0158* (2013.01)

(56) References Cited

U.S. PATENT DOCUMENTS

| | | | |
|---|---|---|---|
| 4,601,283 A | | 7/1986 | Chikama |
| 4,799,474 A | * | 1/1989 | Ueda .................. A61B 1/0058 600/133 |
| 5,191,878 A | * | 3/1993 | Iida .................. A61B 1/00068 600/157 |
| 5,480,029 A | | 1/1996 | Batsford |
| 5,482,029 A | * | 1/1996 | Sekiguchi .......... A61B 1/00039 600/109 |
| 2006/0276689 A1 | * | 12/2006 | Litscher ............. A61B 1/00103 600/156 |

FOREIGN PATENT DOCUMENTS

| | | |
|---|---|---|
| JP | S62-211039 A | 9/1987 |
| JP | H06-70879 A | 3/1994 |
| JP | H06-292652 A | 10/1994 |
| JP | 3122673 B2 | 1/2001 |
| JP | 3142928 B2 | 3/2001 |

OTHER PUBLICATIONS

International Search Report dated Jul. 5, 2016 issued in PCT/JP2016/062241.
English Abstract of JP H05-91971 A, dated Apr. 16, 1993.
English Abstract of JP H05-168586 A, dated Jul. 2, 1993.
Chinese Office Action dated Apr. 21, 2020 in Chinese Patent Application No. 201680084717.6.

* cited by examiner

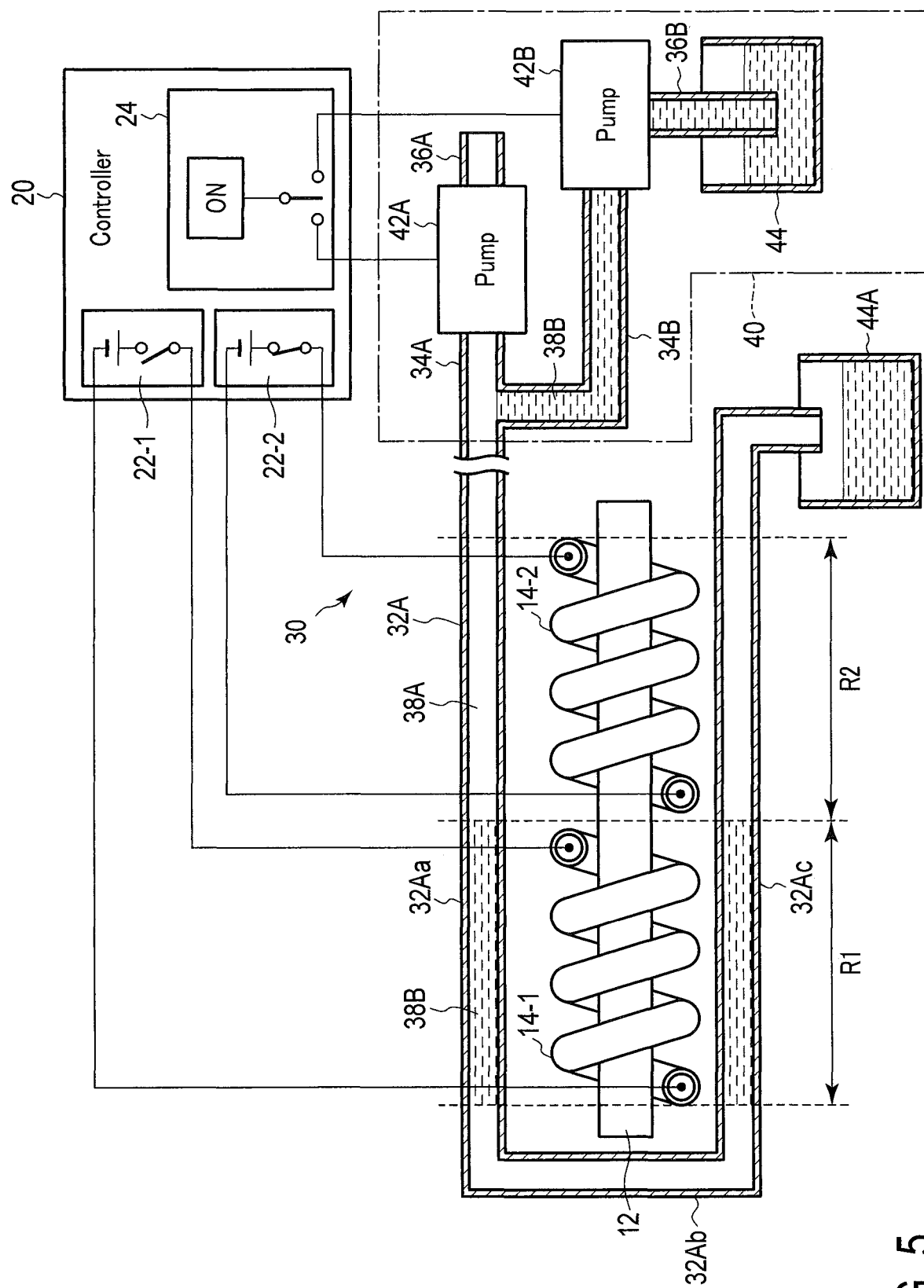
F I G. 5

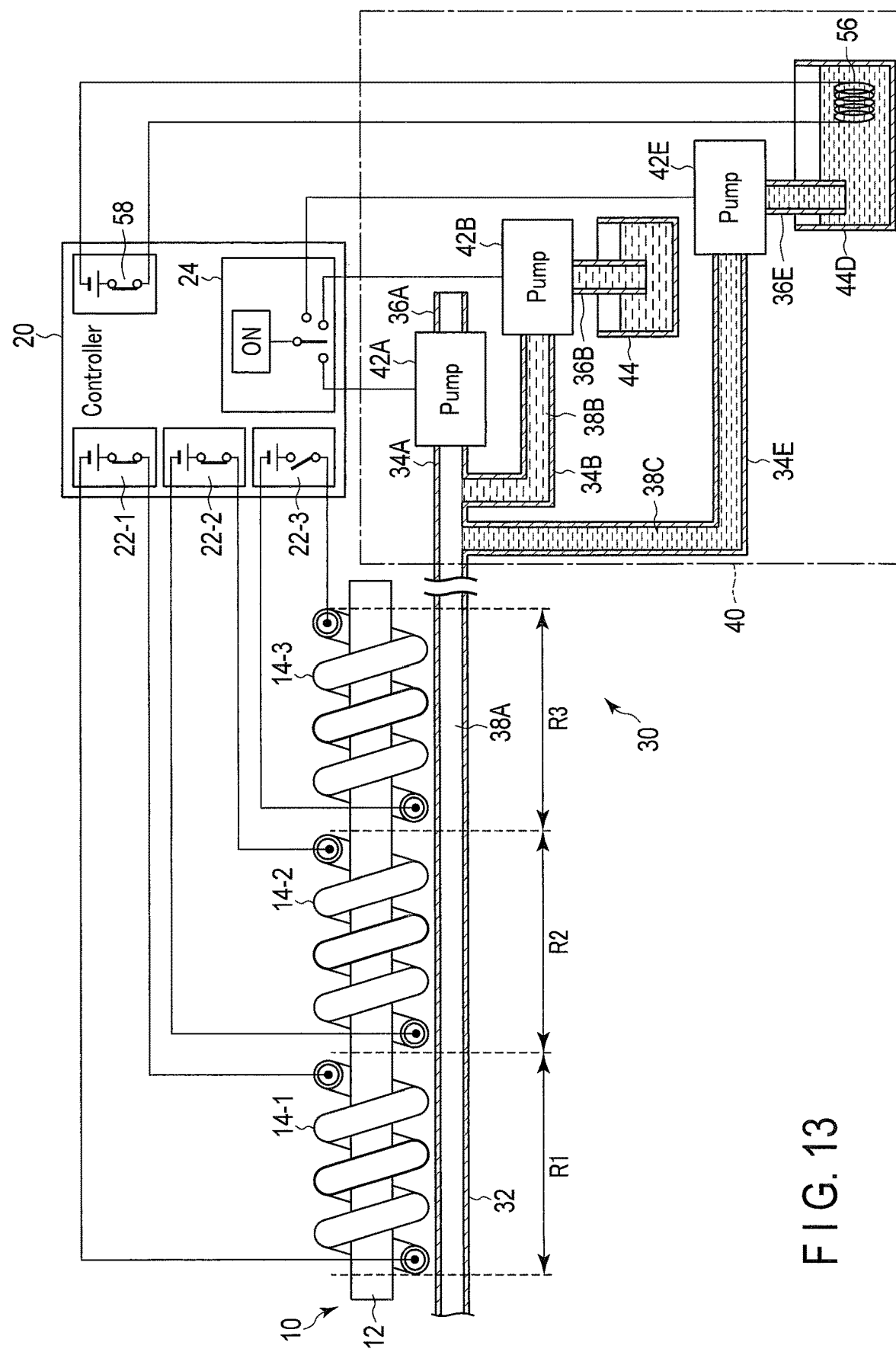
F I G. 13

VARIABLE-STIFFNESS ACTUATOR SYSTEM

CROSS-REFERENCE TO RELATED APPLICATIONS

This application is a Continuation Application of PCT Application No. PCT/JP2016/062241, filed Apr. 18, 2016, the entire contents of which are incorporated herein by reference.

BACKGROUND OF THE INVENTION

1. Field of the Invention

The present invention relates to a variable-stiffness actuator system for varying the stiffness of a flexible member.

2. Description of the Related Art

Japanese Patent No. 3122673 discloses an endoscope capable of varying the stiffness of a flexible section of an insertion section. In this endoscope, both ends of a flexible member (such as a coil pipe) are fixed at predetermined positions in the endoscope, and a flexibility adjustment member (such as a flexibility adjustment wire inserted through a coil pipe) is fixed to the flexible member through a separator. The flexible member and the flexibility adjustment member extend to a handling section along the flexible section and extend almost over the entire flexible section. The flexible member is compressed and stiffened by pulling the flexibility adjustment member, thereby varying the stiffness of the flexible section.

Japanese Patent No. 3142928 discloses a variable-stiffness apparatus for a flexible tube using a shape-memory alloy. The variable-stiffness apparatus includes a coil to be provided in a flexible tube, an electrical insulating tube provided inside the coil, a shape-memory alloyed wire arranged in the electrical insulating tube so as to extend in its axial direction, and an energization heating means for energizing the shape-memory alloyed wire.

The shape-memory alloyed wire has properties of elongating at a low temperature and contracting at a high temperature. The shape-memory alloyed wire extends out through fixed portions at both ends of the coil, and caulking members are fixed to the both ends. The shape-memory alloyed wire is arranged so that it loosens at a low temperature and it tightens up at a high temperature with the caulking members engaged with the fixed portions.

The shape-memory alloyed wire contracts to stiffen the coil at a high temperature at which it becomes energized by the energization heating means. On the other hand, the shape-memory alloyed wire elongates to soften the coil at a low temperature at which it does not is energized.

BRIEF SUMMARY OF THE INVENTION

A variable-stiffness actuator system includes: a shape-memory member, having one end and another end, in which a stiffness increases by being heated and decreases by radiating heat; a heating member, arranged along a longitudinal axis of the shape-memory member, configured to generate heat in response to supply of a current to heat the shape-memory member; a channel arranged along the longitudinal axis of the shape-memory member; a transfer section configured to selectively supply a first heat transmission fluid and a second heat transmission fluid different from the first heat transmission fluid into the channel, and stop the supply of the first heat transmission fluid and the second heat transmission fluid into the channel; and a controller configured to control the transfer section to supply the first heat transmission fluid into the channel and then supply the second heat transmission fluid into the channel, and further to stop the supply of the first heat transmission fluid and the second heat transmission fluid into the channel so that retention of the first heat transmission fluid and retention of the second heat transmission fluid simultaneously occur in the channel.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 shows a variable-stiffness actuator system according to a third embodiment.

FIG. 13 shows a variable-stiffness actuator system according to an eleventh embodiment.

DETAILED DESCRIPTION OF THE INVENTION

First Embodiment

Figure 1:
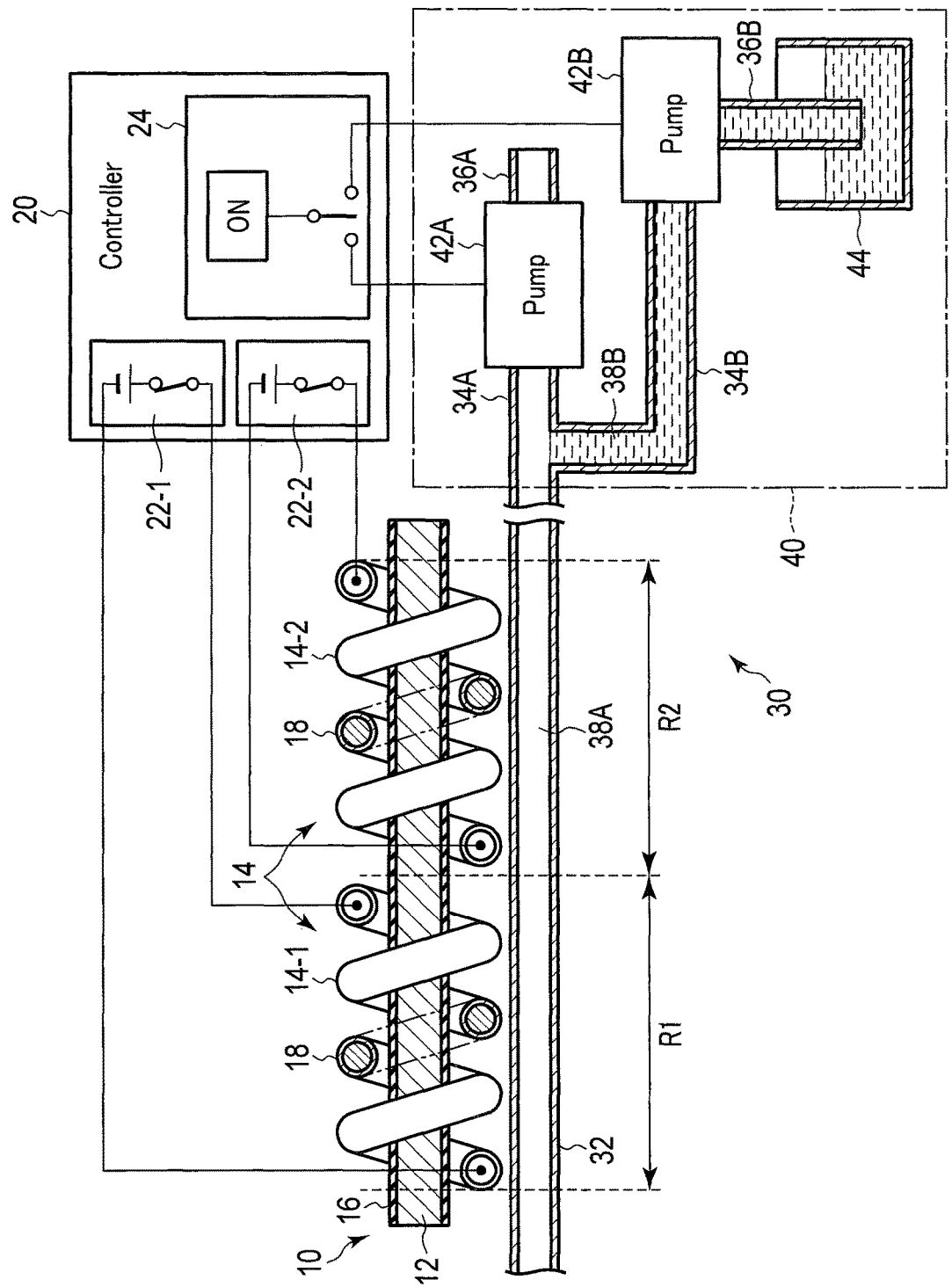
FIG. 1 shows a variable-stiffness actuator system according to a first embodiment.
Figure 2:
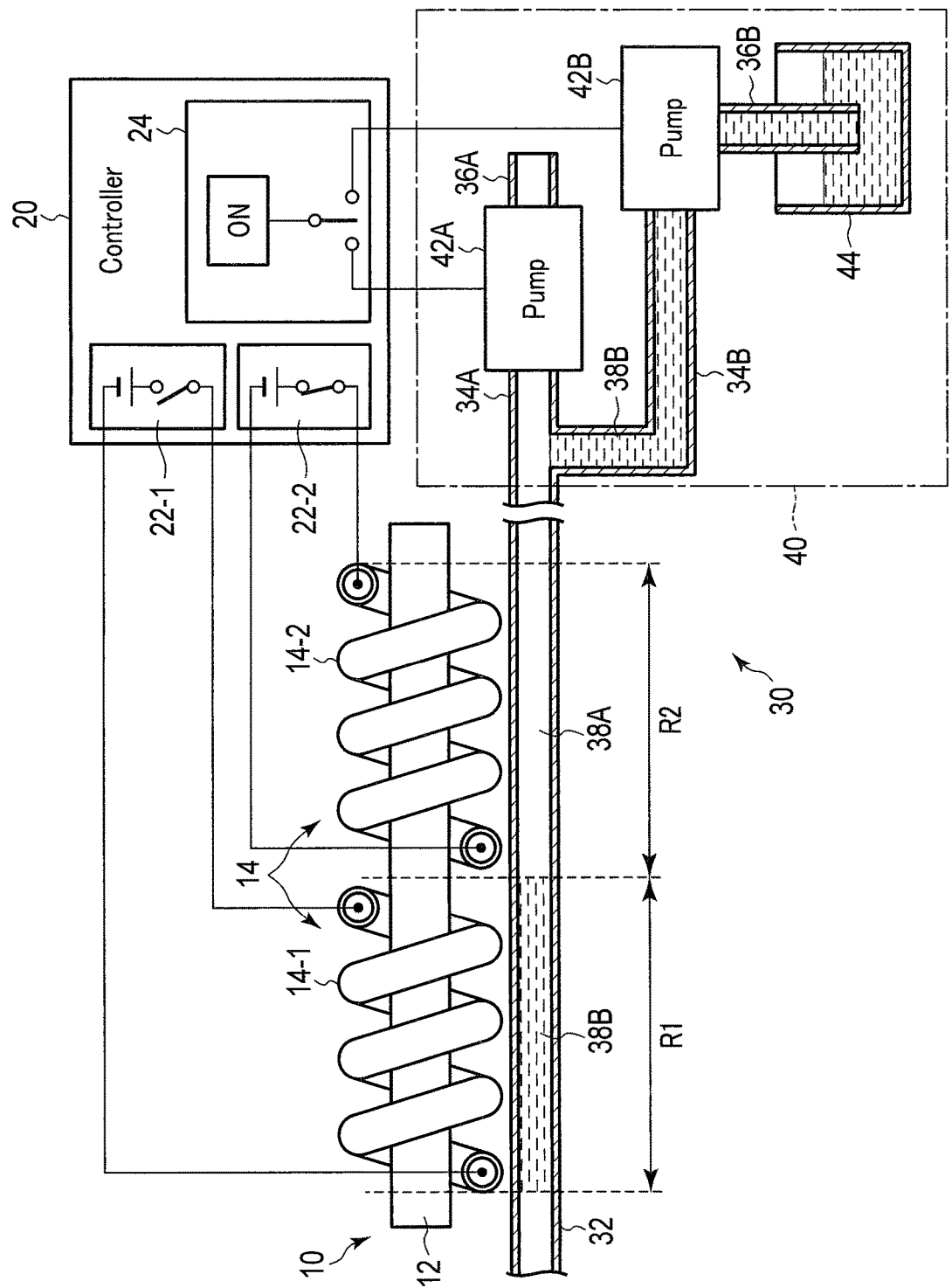
FIG. 2 shows the variable-stiffness actuator system according to the first embodiment.

FIGS. 1 and 2 show a variable-stiffness actuator system according to a first embodiment. As shown in FIGS. 1 and 2, the variable-stiffness actuator system includes a variable-stiffness actuator 10, a heat quantity change promotion system 30 that promotes heat quantity change of the variable-stiffness actuator 10, and a controller 20 that controls the variable-stiffness actuator 10 and the heat quantity change promotion system 30.

The variable-stiffness actuator 10 is to be installed in a flexible member and configured to take different stiffness states so as to have a function of providing different stiffnesses to the flexible member in which the variable-stiffness actuator 10 is installed. The variable-stiffness actuator 10 includes a shape-memory member 12 configured to transit in phase between a first phase and a second phase, and an inducer 14 configured to generate heat in response to supply of a current from the controller 20 to induce transition in phase of the shape-memory member 12 between the first phase and the second phase. The inducer 14 includes inducing members 14-1 and 14-2. The variable-stiffness actuator 10 shown in FIG. 1 includes two inducing members, but is not limited to this, and may include more inducing members.

The shape-memory member 12 is arranged in the flexible member with at least one free end. The shape-memory member 12 takes a low-stiffness state in which it is easily deformable by an external force, i.e., exhibits a low elastic modulus, when it is in the first phase, so as to provide relatively low stiffness to the flexible member. The shape-memory member 12 takes a high-stiffness state in which it tends to take a memorized shape memorized beforehand against an external force, i.e., exhibits a high elastic modulus, when it is in the second phase, so as to provide relatively high stiffness to the flexible member. The memorized shape may be, but is not limited to, a linear shape.

Herein, the external force means a force capable of deforming the shape-memory member 12, and gravity is considered to be part of the external force.

The inducing members 14-1 and 14-2 have the capability of generating heat. The shape-memory member 12 has the property of transiting in phase from the first phase to the second phase in response to heating of the inducing members 14-1 and 14-2.

The shape-memory member 12 may be made of, for example, a shape-memory alloy. The shape-memory alloy may be an alloy including, but not limited to, NiTi, for example. The shape-memory member 12 is not limited to the above, and may also be composed of another material, such as a shape-memory polymer, shape-memory gel, or shape-memory ceramics.

The shape-memory alloy forming the shape-memory member 12 may be, for example, a shape-memory alloy that transits in phase between a martensitic phase and an austenitic phase. In the martensitic phase, the shape-memory alloy is plastically deformed relatively easily by an external force. In other words, the shape-memory alloy exhibits a low elastic modulus in the martensitic phase. In the austenitic phase, the shape-memory alloy is not easily deformed by an external force. Even when the shape-memory alloy is deformed by a greater external force, it exhibits superelasticiy and returns to its memorized shape when the greater external force is lost. In other words, the shape-memory alloy exhibits a high elastic modulus in the austenitic phase.

The inducing members 14-1 and 14-2 are formed by a conductive material, and have the property of generating heat in response to supply of a current. The inducing members 14-1 and 14-2 may be formed by, for example, a heating wire, i.e., a conductive member with large electrical resistance.

The shape-memory member 12 has an elongated appearance shape. Each of the inducing members 14-1 and 14-2 is formed by a member shaped like a wire, and is arranged around the shape-memory member 12. The inducing members 14-1 and 14-2 are arranged at intervals along a longitudinal axis of the shape-memory member 12. Each of the inducing members 14-1 and 14-2 spirally extends around the shape-memory member 12 along the longitudinal axis of the shape-memory member 12 with an appropriate clearance from the shape-memory member 12. This configuration enables efficient conduction of heat generated by the inducing members 14-1 and 14-2 to the shape-memory member 12.

The inducing members 14-1 and 14-2 may comprise the same structure. However, the structure of the inducing members 14-1 and 14-2 is not limited to this, and may include different structures. The different structures may have different lengths, diameters, or pitches, and may be made of different materials. Namely, all or some of the inducing members 14-1 and 14-2 may have the same characteristics or different characteristics.

The shape-memory member 12 may be formed by a conductive material. For example, an insulating film 16 is provided around the shape-memory member 12. The insulating film 16 serves to prevent a short circuit between the shape-memory member 12 and the inducing members 14-1 and 14-2. The insulating film 16 is provided to cover at least a part facing the inducing members 14-1 and 14-2. FIG. 1 shows a configuration in which the outer peripheral surface of the shape-memory member 12 is entirely covered; however, the configuration is not limited to this, and the outer peripheral surface of the shape-memory member 12 may be partly covered, or the shape-memory member 12 may be entirely covered.

Insulating films 18 are provided around the inducing members 14-1 and 14-2. The insulating films 18 serve to prevent a short circuit between the shape-memory member 12 and the inducing members 14-1 and 14-2 and a short circuit between adjacent portions of the inducing members 14-1 and 14-2.

The controller 20 includes drivers 22-1 and 22-2 configured to independently drive the inducing members 14-1 and 14-2, respectively. The both ends of the inducing members 14-1 and 14-2 are electrically connected to the drivers 22-1 and 22-2, respectively. Each of the drivers 22-1 and 22-2 includes a power source and a switch. Each of the drivers 22-1 and 22-2 supplies a current to the inducing members 14-1 and 14-2 in response to an ON operation of the switch, and stops supplying a current to the inducing members 14-1 and 14-2 in response to an OFF operation of the switch, respectively. The inducing members 14-1 and 14-2 generate heat in response to supply of a current.

The variable-stiffness actuator 10 is installed in the flexible member without restricting the shape-memory member 12. For example, the variable-stiffness actuator 10 is arranged in a limited space of the flexible member with a small clearance so that an end or both ends of the shape-memory member 12 are a free end or free ends.

Herein, the limited space means a space of a right size capable of containing the variable-stiffness actuator 10 therein. Thus, even when one of the variable-stiffness actuator 10 and the flexible member is slightly deformed, it can contact the other and provide an external force.

For example, the flexible member may be a tube having an inner diameter slightly larger than the outer diameter of the variable-stiffness actuator 10, and the variable-stiffness actuator 10 may be placed inside the tube. The configuration of the flexible member is not limited to this, and the flexible member only has to have a slightly larger space than the variable-stiffness actuator 10. The flexible member may be, for example, an insertion section of an endoscope.

When the shape-memory member 12 is in the first phase, the variable-stiffness actuator 10 provides relatively low stiffness to the flexible member and is easily deformed by an external force exerted on the flexible member, i.e., a force capable of deforming the shape-memory member 12.

When the shape-memory member 12 is in the second phase, the variable-stiffness actuator 10 provides relatively high stiffness to the flexible member and tends to return to its memorized shape against an external force exerted on the flexible member, i.e., a force capable of deforming the shape-memory member 12.

For example, as the phase of the shape-memory member 12 is switched between the first phase and the second phase by the controller 20, the stiffness of the flexible member is switched.

In addition to switching the stiffness, in a situation where an external force other than the gravity is exerted on the flexible member, the variable-stiffness actuator 10 also functions as a bidirectional actuator that switches the shape of the flexible member. In another situation where no external force other than the gravity is exerted on the flexible member, but the flexible member is deformed in the first phase before the phase of the shape-memory member 12 is switched to the second phase, the variable-stiffness actuator 10 also serves as a unidirectional actuator that returns the shape of the flexible member to the original.

The heat quantity change promotion system 30 includes a channel 32 extending near the variable-stiffness actuator 10, and a transfer section 40, fluidly connected to the channel 32, configured to transfer through the channel 32 a heat transmission medium exchanging a heat quantity with the variable-stiffness actuator 10.

The channel 32 is arranged in parallel to the shape-memory member 12. This is preferable for simplification and miniaturization of the configuration. The channel 32 is arranged in the vicinity of the inducing members 14-1 and 14-2. Alternatively, the channel 32 may be arranged in contact with the inducing members 14-1 and 14-2. An end of the channel 32 is mechanically connected to the transfer section 40. The transfer section 40 has a function of retaining the heat transmission medium at a desired position near the variable-stiffness actuator 10 as necessary.

The heat transmission medium includes at least any one of solid, liquid, gas, and semisolid (gel). The heat transmission medium may contain a mixture of a liquid and a solid, such as a bead. The heat transmission medium includes different heat transmission fluids 38A and 38B. At least one of the heat conductivity and the heat capacity is different between the heat transmission fluids 38A and 38B. At least one of the viscosity and the density is different between the heat transmission fluids 38A and 38B. For example, the heat transmission fluid 38A is composed of gas, and the heat transmission fluid 38B is composed of liquid. As an example, the heat transmission fluid 38A is composed of air, and the heat transmission fluid 38B is composed of water. The heat conductivity of water is approximately 20 times larger than the heat conductivity of air. The heat capacity of water is approximately 3000 times larger than the heat capacity of air.

The transfer section 40 includes pumps 42A and 42B. The pump 42A is for transferring the heat transmission fluid 38A, e.g. air, and the pump 42B is for transferring the heat transmission fluid 38B, e.g. water. The pumps 42A and 42B have a function of suctioning the heat transmission fluids 38A and 38B from suction ports, and discharging the heat transmission fluids 38A and 38B from discharge ports, respectively. The suction port of the pump 42A is connected to an air intake pipe 36A, and the air intake pipe 36A is terminated in the atmosphere. The discharge port of the pump 42A is connected to the channel 32 through a connection channel 34A. The suction port of the pump 42B is connected to a water intake pipe 36B, and the water intake pipe 36B extends into a tank 44 for storing water. The discharge port of the pump 42B is connected to the channel 32 through a connection channel 34B.

The controller 20 includes a pump driver 24 configured to independently drive the pumps 42A and 42B. The pump driver 24 has a function of supplying a signal to one of the pumps 42A and 42B to selectively drive the one of the pumps 42A and 42B. In response to supply of a signal, the pumps 42A and 42B discharge the heat transmission fluids 38A and 38B, respectively. As a result, the transfer section 40 discharges the heat transmission fluids 38A and 38B, which are heat transmission media, into the channel 32. Thereby, the transfer section 40 transfers the heat transmission fluids 38A and 38B through the channel 32 while maintaining a state in which the heat transmission fluids 38A and 38B are separated along the channel 32.

Furthermore, the controller 20 controls the transfer section 40 in conjunction with the control of the inducer 14. Specifically, the controller 20 controls driving of the pumps 42A and 42B in response to the on/off of driving of the inducing members 14-1 and 14-2.

FIG. 1 shows a state in which the inducing members 14-1 and 14-2 are both driven. In this state, it is preferable that the heat quantity of the variable-stiffness actuator 10 is not deprived. Accordingly, the pump driver 24 selectively drives the pump 42A for a predetermined time and then stops the pump 42A in conjunction with the control of the inducing members 14-1 and 14-2, i.e., according to an ON operation of the drivers 22-1 and 22-2. The predetermined time described herein is a time for air as the heat transmission fluid 38A having a volume that fills an internal space of the channel 32 in both of a range R1 in which at least the inducing member 14-1 extends along the shape-memory member 12 and a range R2 in which at least the inducing member 14-2 extends to be transferred by the pump 42A. As a result, air, which is the heat transmission fluid 38A, is retained in the internal space of the channel 32 in both the range R1 and the range R2.

Since the retained air is warmed compared to a flow state, it becomes difficult to deprive the heat of the inducing members 14-1 and 14-2. In addition, since the heat conductivity of air is poor, a heat retaining effect can also be expected.

FIG. 2 shows a state in which the inducing member 14-2 is driven as it is from the state of FIG. 1, but the driving of the inducing member 14-1 is stopped. In this state, in the range R2 corresponding to the inducing member 14-2, it is preferable that the heat quantity of the variable-stiffness actuator 10 is not deprived, while in the range R1 corresponding to the inducing member 14-1, it is preferable that the heat quantity of the variable-stiffness actuator 10 is deprived quickly.

Accordingly, the pump driver 24 selectively drives the pump 42B for a predetermined time and then stops the pump 42B according to an OFF operation of the driver 22-1. The predetermined time described herein is a time for water as the heat transmission fluid 38B having a volume that fills the internal space of the channel 32 in the range R1 corresponding to the inducing member 14-1 to be transferred into the channel 32 by the pump 42B.

Here, it is assumed that the channel 32 extends to a connection portion of each of the connection channels 34A and 34B.

Thereafter, the pump driver 24 selectively drives the pump 42A for a predetermined time and then stops the pump 42A. Thereby, the heat transmission fluids 38A and 38B are transferred in the internal space of the channel 32 while the state in which they are separated along the channel 32 is maintained. The predetermined time described herein is a time for air as the heat transmission fluid 38A having a volume required for water as the heat transmission fluid 38B previously transferred into the channel 32 to be transferred to the range R1 corresponding to the inducing member 14-1 to be transferred into the channel 32 by the pump 42A.

As a result, water as the heat transmission fluid 38B is retained in the internal space of the channel 32 in the range R1, and air as the heat transmission fluid 38A is retained in the internal space of the channel 32 in the range R2.

That is, the transfer section 40 retains the heat transmission fluid 38B, for example water, in the range R1 in which the heat warmed by the inducing member 14-1 should be actively absorbed, and retains the heat transmission fluid 38A, for example air, in the range R2 in which the heat warmed by the inducing member 14-2 should be passively absorbed.

As described above, the heat conductivity of water as the heat transmission fluid 38B is larger than the heat conductivity of air as the heat transmission fluid 38A. In addition, the heat capacity of water as the heat transmission fluid 38B is larger than the heat capacity of air as the heat transmission fluid 38A. Therefore, the retained water quickly deprives the heat quantity of a portion of the variable-stiffness actuator 10 in the range R1. In other words, the retained water promotes heat radiation of the portion of the variable-stiffness actuator 10 in the range R1. Thus, the temperature of the portion of the variable-stiffness actuator 10 in the range R1 corresponding to the inducing member 14-1 in which heat generation is stopped quickly decreases. As a result, a time required for the transition in phase of the shape-memory member 12 from the high-stiffness state of the second phase, for example the austenite phase, to the low-stiffness state of the first phase, for example the martensitic phase, is shortened compared to a case of the absence of the heat quantity change promotion system 30. Thereby, it can be achieved to shorten the transition time from the high-stiffness state to the low-stiffness state of the portion of the variable-stiffness actuator 10 in the range R1.

Here, an example of the operation of selectively and quickly cooling the portion of the variable-stiffness actuator 10 in the range R1 corresponding to the inducing member 14-1 has been described. However, by applying the similar operation, it is possible to selectively and quickly cool the portion of the variable-stiffness actuator 10 in the range R2 corresponding to the inducing member 14-2.

The transfer section 40 discharges unnecessary heat transmission fluids 38A and 38B out of the flexible member in which the variable-stiffness actuator 10 is installed, as necessary, for example, at the time of the next switching of the stiffness. In a case where the flexible member is an insertion section of a medical endoscope, the heat transmission fluids 38A and 38B are composed of a substance that is harmless to the living body, for example, physiological saline, and are discharged at a temperature that does not adversely affect the living body.

Second Embodiment

Figure 3:
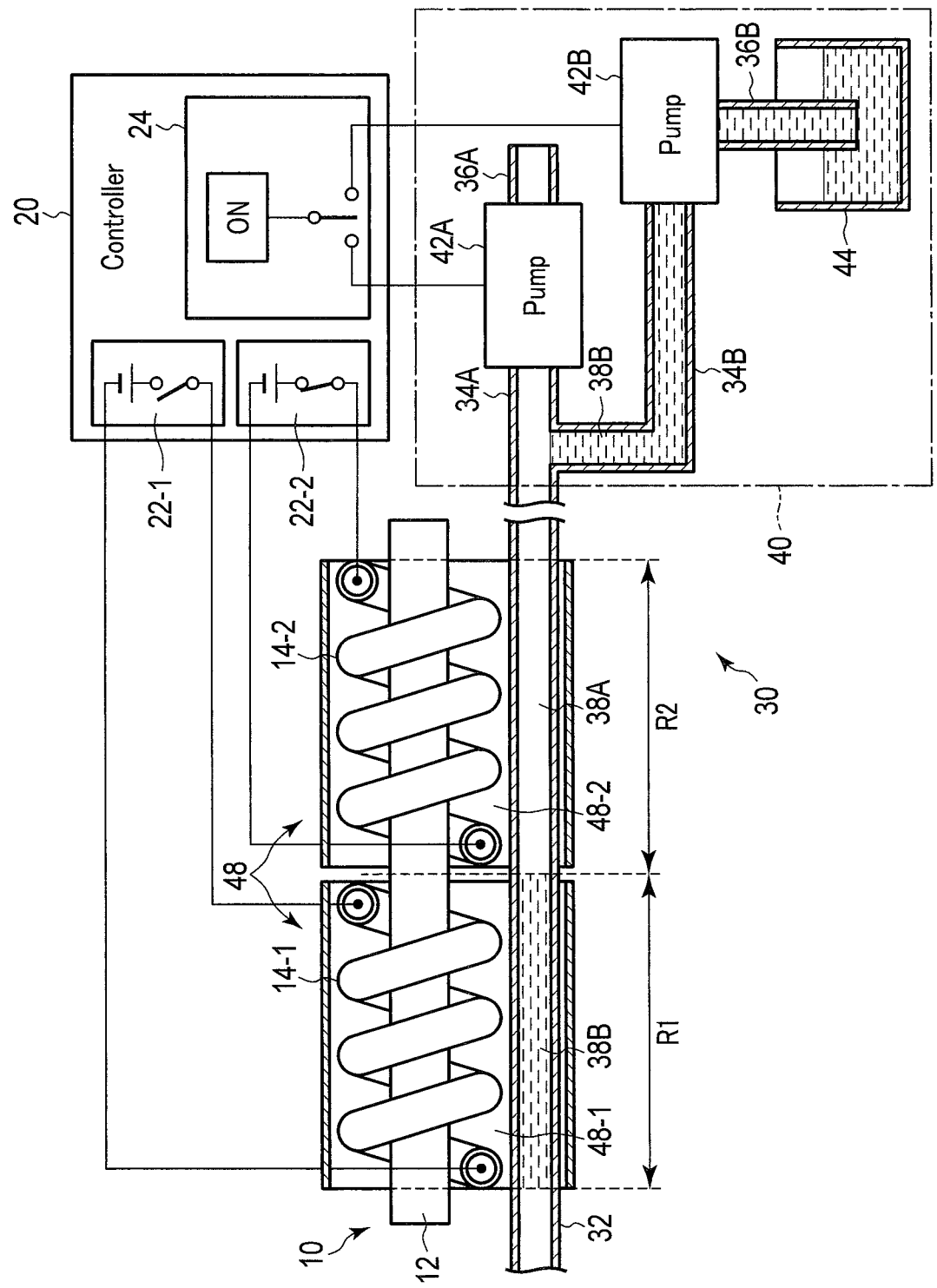
FIG. 3 shows a variable-stiffness actuator system according to a second embodiment.
Figure 4:
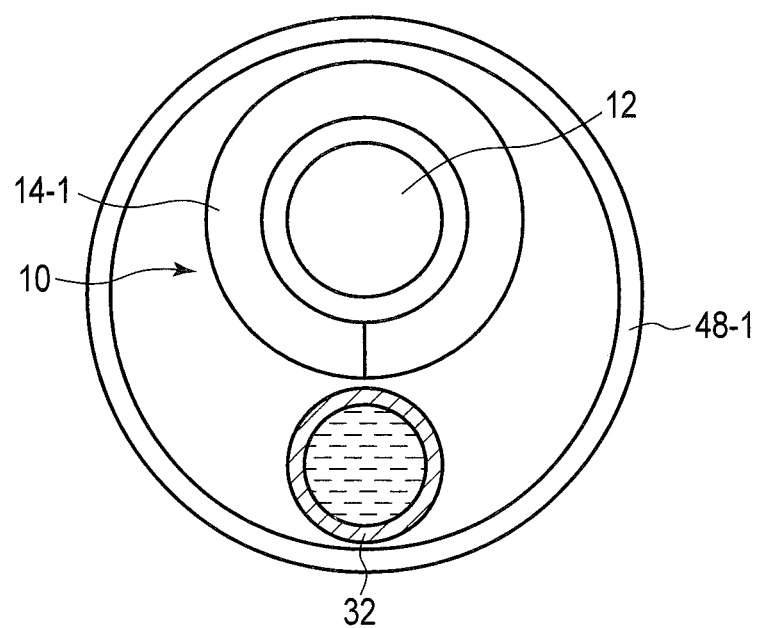
FIG. 4 is a side view of a peripheral portion of the variable-stiffness actuator shown in FIG. 3.

FIG. 3 shows a variable-stiffness actuator system according to a second embodiment. In addition, FIG. 4 is a side view of a peripheral portion of the variable-stiffness actuator shown in FIG. 3. In FIGS. 3 and 4, members denoted by the same reference numerals as those shown in FIGS. 1 and 2 are similar members, and a detailed description thereof will be omitted. Hereinafter, the description will focus on different portions. That is, portions not mentioned in the following description are the same as those in the first embodiment.

The variable-stiffness actuator system of the present embodiment has a configuration in which a heat transmission promoter 48 configured to promote heat transmission between the variable-stiffness actuator 10 and the channel 32 is added to the variable-stiffness actuator system of the first embodiment. The heat transmission promoter 48 is provided around the variable-stiffness actuator 10 and the channel 32. The heat transmission promoter 48 includes heat transmission members 48-1 and 48-2. The heat transmission member 48-1 surrounds the variable-stiffness actuator 10 and the channel 32 in the range R1 corresponding to the inducing member 14-1, and the heat transmission member 48-2 surrounds the variable-stiffness actuator 10 and the channel 32 in the range R2 corresponding to the inducing member 14-2. In this way, by arranging the separate heat transmission members 48-1 and 48-2 for the range R1 and the range R2, an effect on portions of the shape-memory member 12 that are located in the adjacent and different ranges R1 and R2 is reduced.

The heat transmission members 48-1 and 48-2 are preferably composed of a material having high heat conductivity. The heat transmission members 48-1 and 48-2 are preferably arranged adjacent to the inducing members 14-1 and 14-2 and the channel 32, respectively.

In FIGS. 3 and 4, the heat transmission members 48-1 and 48-2 are depicted as a single cylinder, but are not limited to such a form. The heat transmission members 48-1 and 48-2 may be preferably composed of a gel-like grease, a sheet-like metal foil, a carbon-based sheet, or the like. Furthermore, the heat transmission members 48-1 and 48-2 may be composed by using gel and sheet together. For example, a configuration may be adopted in which a gel is filled in the space inside the heat transmission member 48-1 shown in FIG. 4.

In the present embodiment, since the heat transmission promoter 48, that is, the heat transmission members 48-1 and 48-2 are arranged around the variable-stiffness actuator 10 and the channel 32, heat transmission efficiency is improved compared to the first embodiment. This increases the efficiency of heat transmission between the shape-memory member 12 and the channel 32, and promotes the transition from the high-stiffness state to the low-stiffness state. In addition, the efficiency of heat transmission between the inducing members 14-1 and 14-2 and the shape-memory member 12 is increased, and the transition from the low-stiffness state to the high-stiffness state is promoted.

Third Embodiment

FIG. 5 shows a variable-stiffness actuator system according to a third embodiment. In FIG. 5, members denoted by the same reference numerals as those shown in FIGS. 1 and 2 are similar members, and a detailed description thereof will be omitted. Hereinafter, the description will focus on different portions. That is, portions not mentioned in the following description are the same as those in the first embodiment.

In the variable-stiffness actuator system of the present embodiment, the heat quantity change promotion system 30 includes a channel 32A instead of the channel 32 of the first embodiment, and also includes a tank 44A configured to receive water as the heat transmission fluid 38B discharged from the channel 32A.

The channel 32A extends forward and backward along the variable-stiffness actuator 10. In other words, the channel 32A includes a forward channel part 32Aa extending along the variable-stiffness actuator 10, a backward channel part 32Ac extending along the variable-stiffness actuator 10, and a folded-back channel part 32Ab connecting the forward channel part 32Aa and the backward channel part 32Ac. The forward channel part 32Aa and the backward channel part 32Ac are arranged in the vicinity of the variable-stiffness actuator 10. The forward channel part 32Aa and the backward channel part 32Ac are arranged adjacent to the inducing members 14-1 and 14-2. Alternatively, the forward channel part 32Aa and the backward channel part 32Ac may be arranged in contact with the inducing members 14-1 and 14-2.

In the present embodiment, for example, in a case of selectively causing the portion of the variable-stiffness actuator 10 in the range R1 corresponding to the inducing member 14-1 to be in the low-stiffness state from the high-stiffness state, the pump driver 24 selectively drives the pump 42B for a predetermined time and then stops the pump 42B according to an OFF operation of the driver 22-1. The predetermined time described herein is a time for water as the heat transmission fluid 38B having a volume that fills an internal space of the channel 32A within the range R1 corresponding to the inducing member 14-1 to be transferred into the channel 32A by the pump 42B.

Next, the pump driver 24 selectively drives the pump 42A for a predetermined time, and then stops the pump 42A. The predetermined time described herein is a time for air as the heat transmission fluid 38A having a volume that fills an internal space of the channel 32A between the range R1 and the range R1, i.e. the folded-back channel part 32Ab, to be transferred into the channel 32A by the pump 42A.

Subsequently, the pump driver 24 selectively drives the pump 42B for a predetermined time, and then stops the pump 42B. The predetermined time described herein is a time for water as the heat transmission fluid 38B having a volume that fills an internal space of the channel 32A within the range R1 corresponding to the inducing member 14-1 to be transferred into the channel 32A by the pump 42B.

Thereafter, the pump driver 24 selectively drives the pump 42A for a predetermined time, and then stops the pump 42A. The predetermined time described herein is a time for air as the heat transmission fluid 38A having a volume required for water as the heat transmission fluid 38B previously transferred into the channel 32A to be transferred to the range R1 corresponding to the inducing member 14-1 to be transferred into the channel 32A by the pump 42A.

As a result, in the vicinity of the variable-stiffness actuator 10, water as the heat transmission fluid 38B is retained in the internal space of the channel 32A in the range R1, and air as the heat transmission fluid 38A is retained in the internal space of the channel 32A in the range R2. Thereby, it is achieved to shorten the transition time from the high-stiffness state to the low-stiffness state of the portion of the variable-stiffness actuator 10 within the range R1.

The air as the heat transmission fluid 38A and the water as the heat transmission fluid 38B fed into the channel 32A are discharged from a tip end of the channel 32A. The water as the heat transmission fluid 38B discharged from the channel 32A is collected in the tank 44A.

In the present embodiment, since the forward channel part 32Aa and the backward channel part 32Ac of the channel 32A are arranged in the vicinity of the variable-stiffness actuator 10, the heat radiation efficiency is improved compared to the first embodiment.

Herein, when retaining the water as the heat transmission fluid 38B in the internal space of the channel 32A within the range R1 and the range R2, the air as the heat transmission fluid 38A is retained in the internal space of the channel 32A between the range R1 and the range R1, i.e. the folded-back channel part 32Ab, but the water as the heat transmission fluid 38B may also be retained in the internal space of the channel 32A between the range R1 and the range R1, i.e. the folded-back channel part 32Ab.

FIG. 5 depicts the tank 42 and the tank 44A as separate tanks, but the tank 42 and the tank 44A may be replaced by a single tank with which the heat transmission fluid 38B is circulated.

Fourth Embodiment

Figure 6:
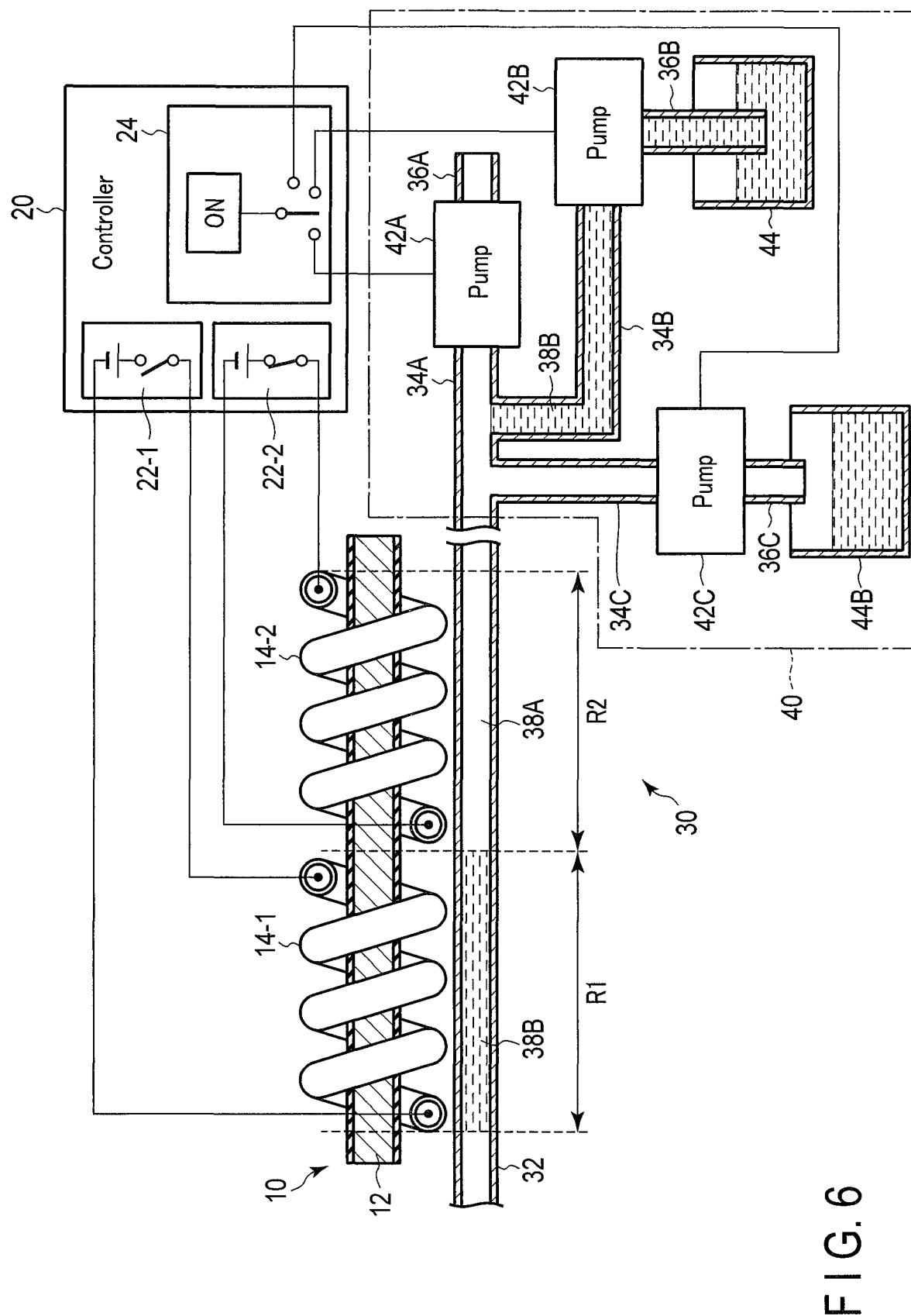
FIG. 6 shows a variable-stiffness actuator system according to a fourth embodiment.

FIG. 6 shows a variable-stiffness actuator system according to a fourth embodiment. In FIG. 6, members denoted by the same reference numerals as those shown in FIGS. 1 and 2 are similar members, and a detailed description thereof will be omitted. Hereinafter, the description will focus on different portions. That is, portions not mentioned in the following description are the same as those in the first embodiment.

The variable-stiffness actuator system of the present embodiment is configured such that a pump 42C configured to suction the heat transmission fluids 38A and 38B is added to the variable-stiffness actuator system of the first embodiment. That is, in addition to the function of discharging the heat transmission fluids 38A and 38B into the channel 32, the transfer section 40 has a function of suctioning the heat transmission fluids 38A and 38B from the channel 32.

A suction port of the pump 42C is connected to the channel 32 through a connection channel 34C. A discharge port of the pump 42C is connected to a discharge pipe 36C, and the discharge pipe 36C extends into a tank 44B for storing water.

In the present embodiment, the heat transmission fluid 38A, for example air, and the heat transmission fluid 38B, for example water, fed into the channel 32 are suctioned by the pump 42C, and are discharged through the discharge pipe 36C. The heat transmission fluid 38B, for example water, is collected in the tank 44B.

Fifth Embodiment

Figure 7:
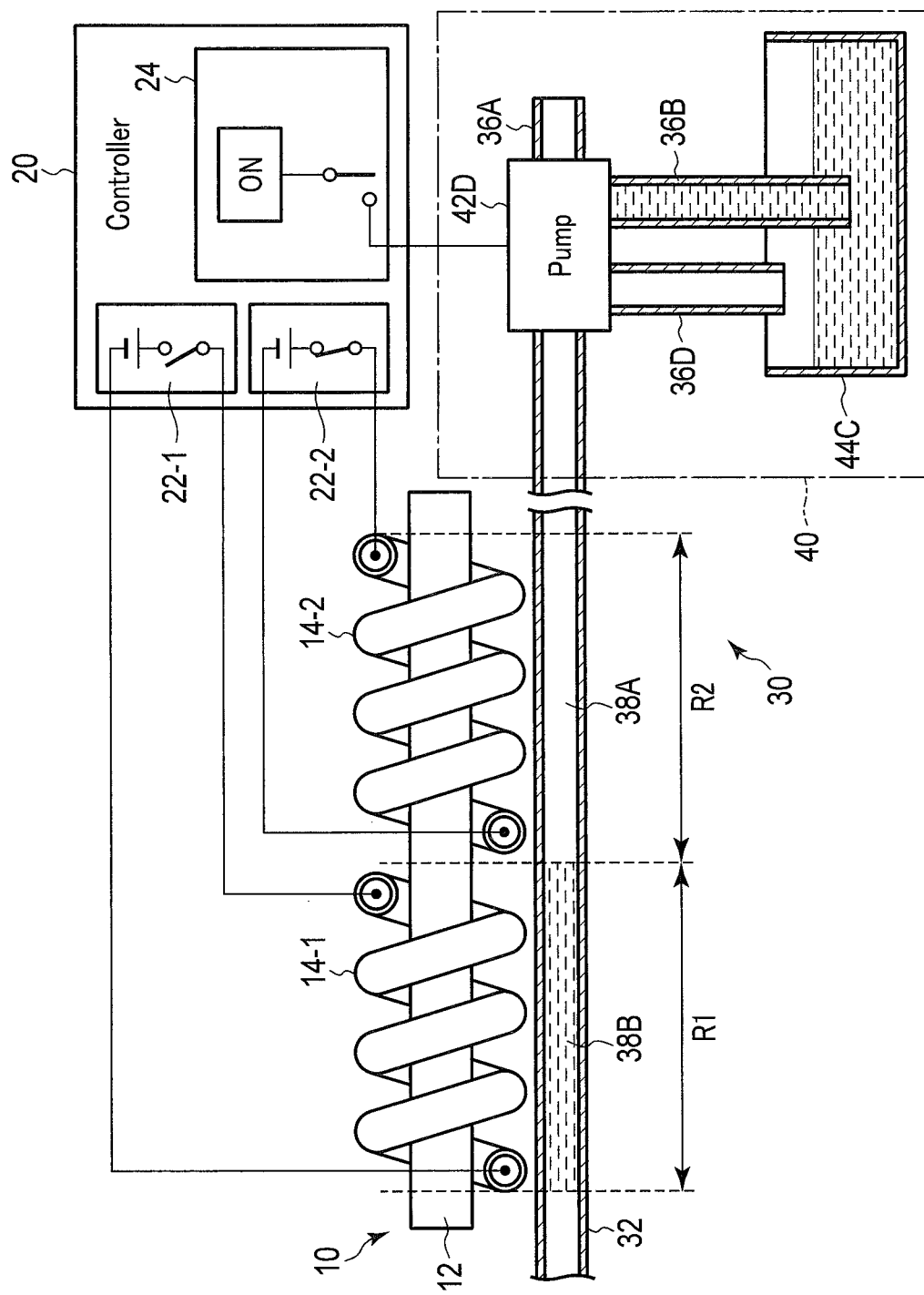
FIG. 7 shows a variable-stiffness actuator system according to a fifth embodiment.

FIG. 7 shows a variable-stiffness actuator system according to a fifth embodiment. In FIG. 7, members denoted by the same reference numerals as those shown in FIGS. 1, 2, and 6 are similar members, and a detailed description thereof will be omitted. Hereinafter, the description will focus on different portions. That is, portions not mentioned in the following description are the same as those in the first and fourth embodiments.

In the variable-stiffness actuator system of the present embodiment, the transfer section 40 includes a pump 42D instead of the pumps 42A and 42B of the first embodiment, and includes a tank 44C instead of the tank 44 and the tank 44B.

In addition to the function of discharging the heat transmission fluids 38A and 38B into the channel 32, the pump 42D has a function of suctioning the heat transmission fluids 38A and 38B from the channel 32. The pump 42D has a function of suctioning the heat transmission fluid 38A from a first suction port and discharging the heat transmission fluid 38A from a discharge suction port, a function of suctioning the heat transmission fluid 38B from a second suction port and discharging the heat transmission fluid 38B from the discharge suction port, and a function of suctioning the heat transmission fluids 38A and 38B from the discharge suction port and discharging the heat transmission fluids 38A and 38B from a discharge port.

The first suction port of the pump 42D is connected to the air intake pipe 36A, and the air intake pipe 36A is terminated in the atmosphere. The second suction port of the pump 42D is connected to the water intake pipe 36B, and the water intake pipe 36B extends into the tank 44C for storing the heat transmission fluid 38B. The discharge suction port of the pump 42D is directly connected to the channel 32. The discharge port of the pump 42D is connected to a discharge pipe 36D, and the discharge pipe 36D extends into the tank 44C.

In the present embodiment, the heat transmission fluids 38A and 38B are collected in the tank 44C, and are not discharged out of the flexible member in which the variable-stiffness actuator 10 is installed. In the configuration in which the heat transmission fluids 38A and 38B are discharged out of the flexible member and in a case where the flexible member is an insertion section of a medical endoscope, the heat transmission fluids 38A and 38B are required to be composed of a substance that is harmless to the living body and discharged at a temperature that does not adversely affect the living body. In contrast, the variable-stiffness actuator system of the present embodiment is configured such that the heat transmission fluids 38A and 38B are not discharged out of the flexible member, so that such restrictions are not required for the heat transmission fluids 38A and 38B.

Sixth Embodiment

Figure 8:
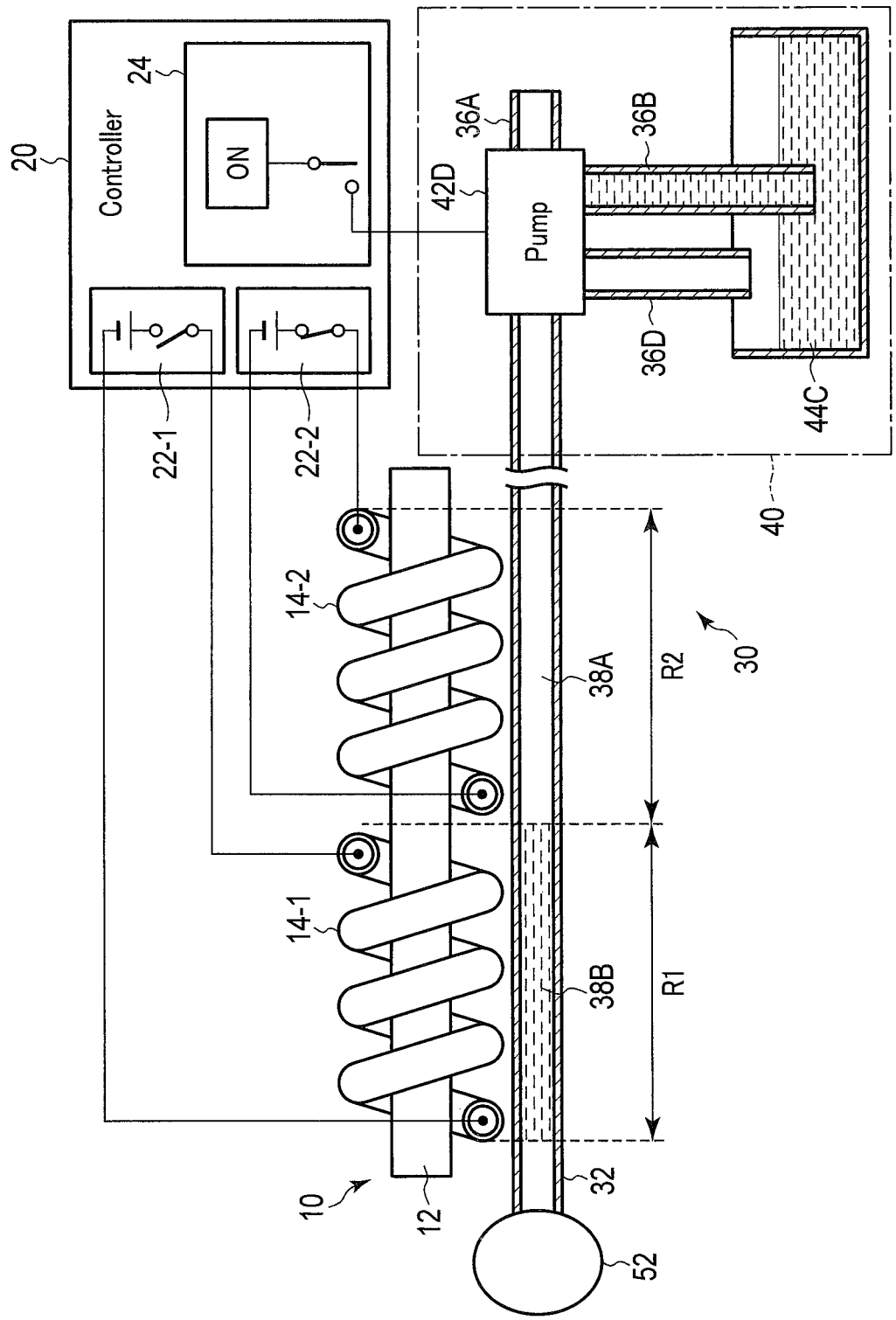
FIG. 8 shows a variable-stiffness actuator system according to a sixth embodiment.

FIG. 8 shows a variable-stiffness actuator system according to a sixth embodiment. In FIG. 8, members denoted by the same reference numerals as those shown in FIGS. 1, 2, and 7 are similar members, and a detailed description thereof will be omitted. Hereinafter, the description will focus on different portions. That is, portions not mentioned in the following description are the same as those in the first and fifth embodiments.

The variable-stiffness actuator system of the present embodiment is configured such that a storage section 52 configured to store the heat transmission media 38A and 38B is added to the variable-stiffness actuator system of the fifth embodiment. The storage section 52 is provided at an end on an opposite side of an end of the channel 32 to which the transfer section 40 is connected. The storage section 52 preferably expands and contracts according to an internal pressure.

In the variable-stiffness actuator system of the fifth embodiment, in a case where the end of the channel 32 on the opposite side of the pump 42D is not sealed, there is a concern that the heat transmission fluids 38A and 38B may unintentionally leak into the flexible member from the channel 32. In addition, in a case where the end of the channel 32 on the opposite side of the pump 42D is sealed, when the heat transmission fluids 38A and 38B are fed into the channel 32, there is a concern that the internal portion of the channel 32 becomes high pressure, and troubles may occur in transferring of the heat transmission fluids 38A and 38B.

In the variable-stiffness actuator system of the present embodiment, since the storage section 52 is provided at the end of the channel 32 on the opposite side of the pump 42D, it is prevented that the heat transmission fluids 38A and 38B unintentionally leak into the flexible member from the channel 32.

The storage section 52 preferably expands and contracts according to the internal pressure. As the pressure inside the channel 32 increases, the storage section 52 expands, and as the pressure inside the channel 32 decreases, the storage section 52 contracts. Thus, the pressure inside the channel 32 is kept substantially constant. Thereby, the internal portion of the channel 32 is prevented from becoming high pressure when the high-pressure heat transmission fluids 38A and 38B are fed into the channel 32 so that effective transferring of the heat transmission fluids 38A and 38B is secured.

Seventh Embodiment

Figure 9:
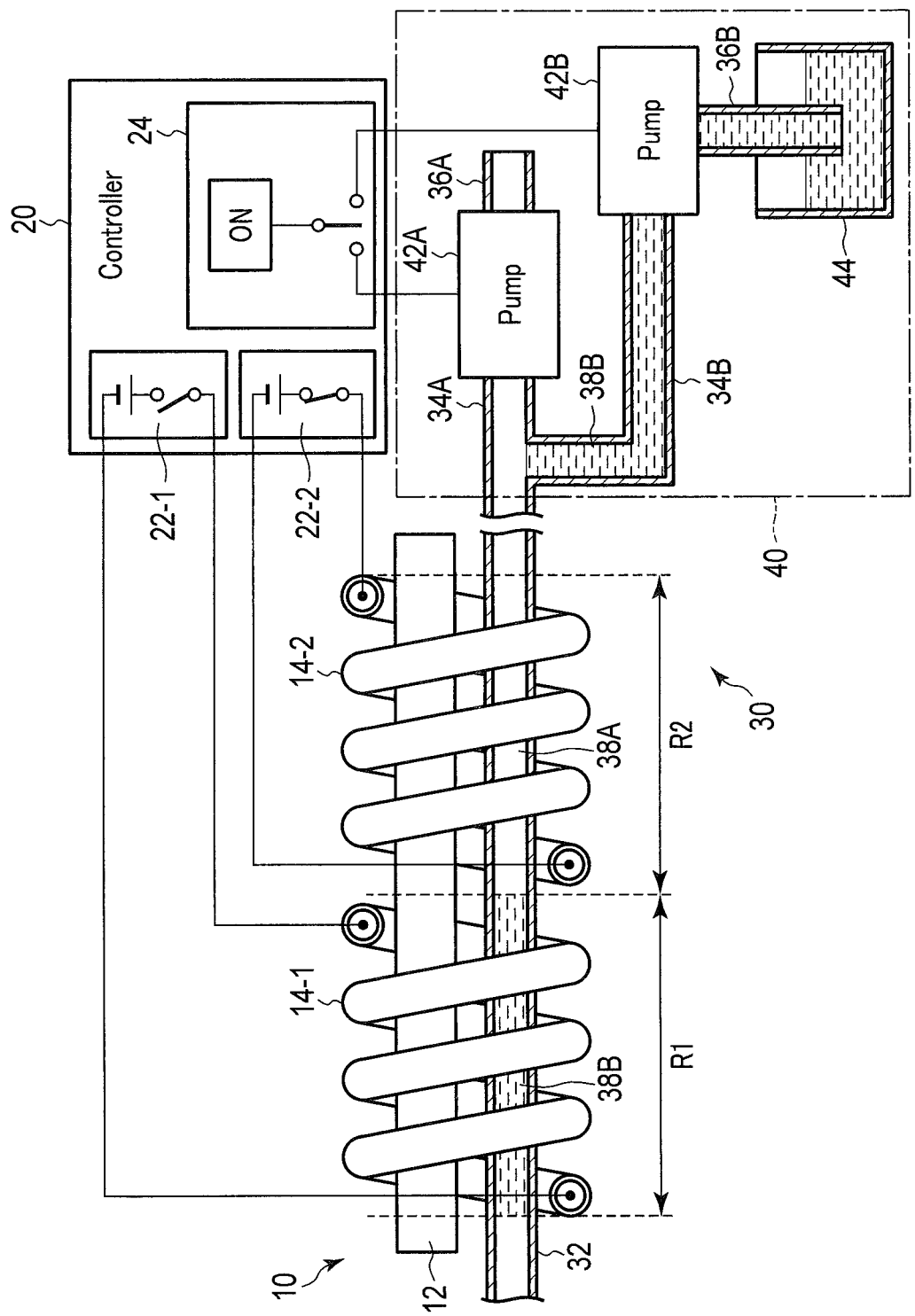
FIG. 9 shows a variable-stiffness actuator system according to a seventh embodiment.

FIG. 9 shows a variable-stiffness actuator system according to a seventh embodiment. In FIG. 9, members denoted by the same reference numerals as those shown in FIGS. 1 and 2 are similar members, and a detailed description thereof will be omitted. Hereinafter, the description will focus on different portions. That is, portions not mentioned in the following description are the same as those in the first embodiment.

The variable-stiffness actuator system of the present embodiment differs from the variable-stiffness actuator system of the first embodiment in the point of the layout of the channel 32 and the inducing members 14-1 and 14-2. In the first embodiment, the channel 32 is arranged outside the variable-stiffness actuator 10, and extends outside the inducing members 14-1 and 14-2. In the present embodiment, however, the channel 32 is arranged adjacent to the shape-memory member 12 of the variable-stiffness actuator 10, and extends on an inner side of the inducing members 14-1 and 14-2.

In the present embodiment, since the channel 32 is arranged adjacent to the shape-memory member 12, when switched from the high-stiffness state to the low-stiffness state, the effect of promoting the heat radiation of the shape-memory member 12 is improved. This further shortens the transition time of the variable-stiffness actuator 10 from the high-stiffness state to the low-stiffness state.

Eighth Embodiment

Figure 10:
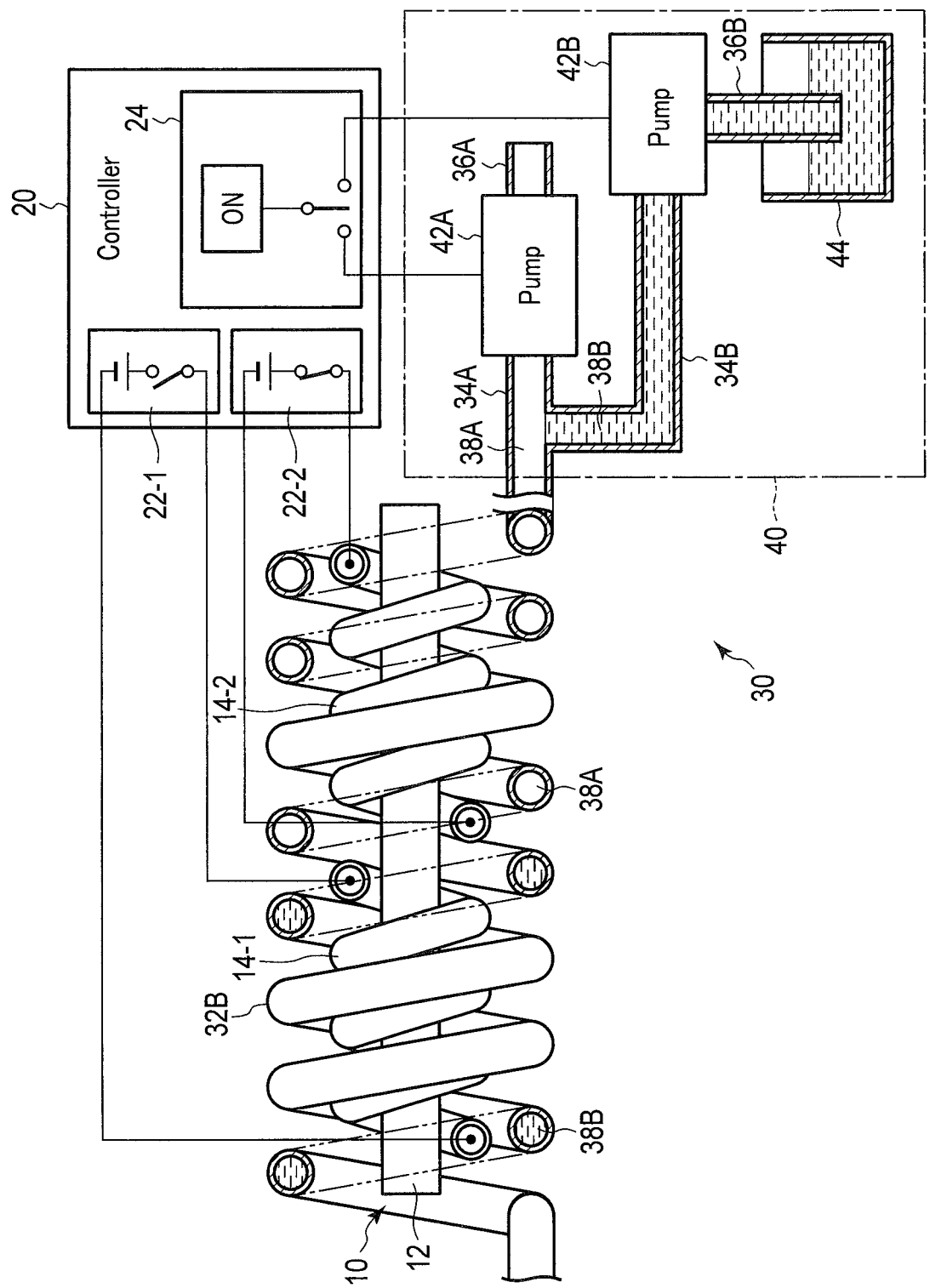
FIG. 10 shows a variable-stiffness actuator system according to an eighth embodiment.

FIG. 10 shows a variable-stiffness actuator system according to an eighth embodiment. In FIG. 10, members denoted by the same reference numerals as those shown in FIGS. 1 and 2 are similar members, and a detailed description thereof will be omitted. Hereinafter, the description will focus on different portions. That is, portions not mentioned in the following description are the same as those in the first embodiment.

In the variable-stiffness actuator system of the present embodiment, the heat quantity change promotion system 30 includes a channel 32B instead of the channel 32 of the first embodiment.

The channel 32B surrounds the inducers 14-1 and 14-2, and spirally extends around the entire inducers 14-1 and 14-2. The channel 32B is arranged adjacent to the inducers 14-1 and 14-2. Alternatively, the channel 32B may be arranged in contact with the inducers 14-1 and 14-2.

In the variable-stiffness actuator system of the present embodiment, since the channel 32B spirally extends around the inducers 14-1 and 14-2, a total area of adjacent portions or contacting portions of the channel 32B and the inducers 14-1 and 14-2 is much greater than a total area of adjacent portions or contacting portions of the channel 32 and the inducers 14-1 and 14-2 of the variable-stiffness actuator system of the first embodiment.

Thus, when switched from the high-stiffness state to the low-stiffness state, the effect of promoting the heat radiation of the shape-memory member 12 is improved. This further shortens the transition time of the variable-stiffness actuator 10 from the high-stiffness state to the low-stiffness state.

In addition, when switched from the low-stiffness state to the high-stiffness state, since the heat transmission fluid 38A having a low heat conductivity or heat capacity is retained in the internal portion of the channel 32, a heat insulating effect to the periphery of the variable-stiffness actuator 10 can also be expected.

Here, although the channel 32B spirally extends around the entire inducers 14-1 and 14-2, the channel 32B may spirally extend so as to be wound around the inducers 14-1 and 14-2.

Ninth Embodiment

Figure 11:
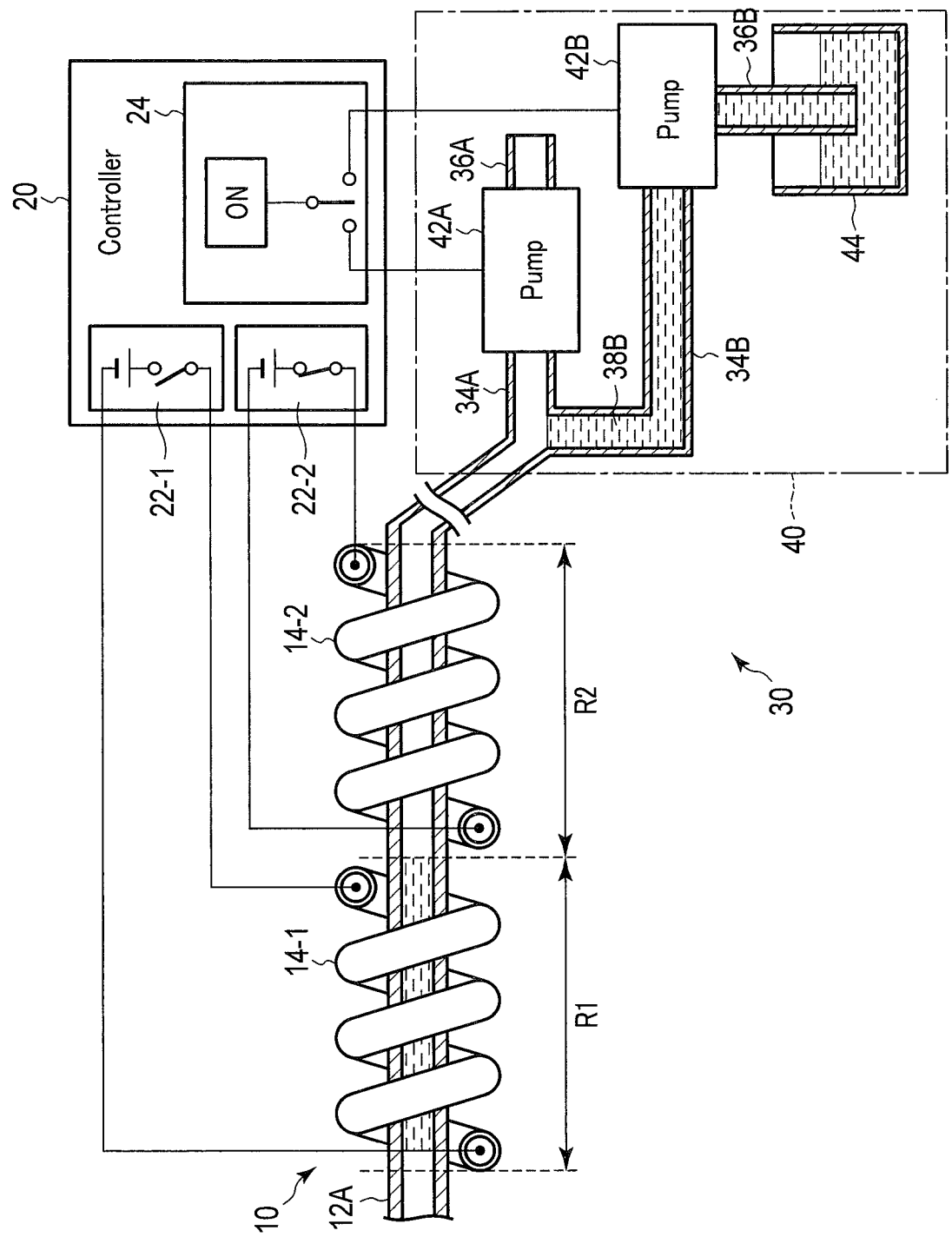
FIG. 11 shows a variable-stiffness actuator system according to a ninth embodiment.

FIG. 11 shows a variable-stiffness actuator system according to a ninth embodiment. In FIG. 11, members denoted by the same reference numerals as those shown in FIGS. 1 and 2 are similar members, and a detailed description thereof will be omitted. Hereinafter, the description will focus on different portions. That is, portions not mentioned in the following description are the same as those in the first embodiment.

The variable-stiffness actuator system of the present embodiment includes a shape-memory member 12A instead of the shape-memory member 12 and the channel 32 of the first embodiment. The shape-memory member 12A is cylindrical-shaped, and also serves as a channel for the heat transmission fluids 38A and 38B. The shape-memory member 12A extends through the inner side of the inducing members 14-1 and 14-2. The shape-memory member 12A is connected to the pump 42A through the connection channel 34A, and is connected to the pump 42B through the connection channel 34B. Such a configuration contributes to miniaturization of the variable-stiffness actuator system to be installed in the flexible member.

In the variable-stiffness actuator system of the present embodiment, the heat transmission fluids 38A and 38B are in direct contact with the shape-memory member 12A. Thus, when switched from the high-stiffness state to the low-stiffness state, since the heat transmission fluid 38B having a high heat conductivity or heat capacity is retained in an internal portion of the shape-memory member 12A, the effect of promoting the heat radiation of the shape-memory member 12A is improved. This further shortens the transition time of the variable-stiffness actuator 10 from the high-stiffness state to the low-stiffness state.

A configuration in which the shape-memory member is molded into a cylindrical shape and also serves as a channel as described above may be applied to other embodiments. For example, the configuration may be applied to the forward channel part 32Aa or the backward channel part 32Ac of the channel 32A of the third embodiment shown in FIG. 5, or may be applied to both the forward channel part 32Aa and the backward channel part 32Ac of the channel 32A of the third embodiment.

Tenth Embodiment

Figure 12:
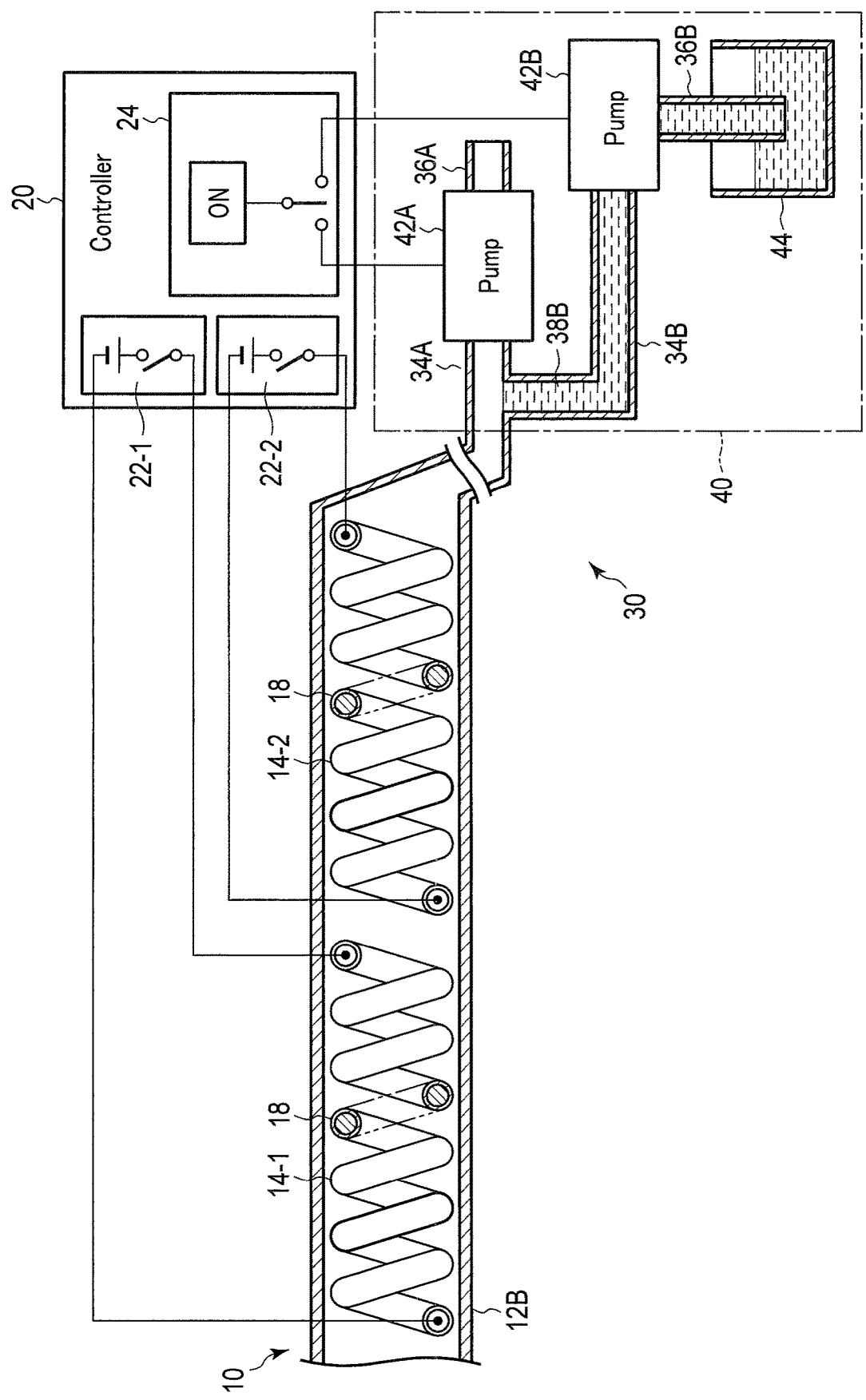
FIG. 12 shows a variable-stiffness actuator system according to a tenth embodiment.

FIG. 12 shows a variable-stiffness actuator system according to a tenth embodiment. In FIG. 12, members denoted by the same reference numerals as those shown in FIGS. 1 and 2 are similar members, and a detailed description thereof will be omitted. Hereinafter, the description will focus on different portions. That is, portions not mentioned in the following description are the same as those in the first embodiment.

The variable-stiffness actuator system of the present embodiment includes a shape-memory member 12B instead of the shape-memory member 12 and the channel 32 of the first embodiment. The shape-memory member 12B is cylindrical-shaped, and also serves as a channel for the heat transmission fluids 38A and 38B. The shape-memory member 12B is connected to the pump 42A through the connection channel 34A, and is connected to the pump 42B through the connection channel 34B. The inducing members 14-1 and 14-2 are arranged in a cavity of the shape-memory member 12B. Such a configuration contributes to miniaturization of the variable-stiffness actuator system to be installed in the flexible member. In addition, an effect that the heat generated by the inducing members 14-1 and 14-2 is less likely to be transmitted to the periphery of the variable-stiffness actuator 10 can be expected.

The heat transmission fluids 38A and 38B are preferably composed of an insulator. As a result, even if an insulating film 18 provided around the inducing members 14-1 and 14-2 is damaged, a short circuit is prevented.

Eleventh Embodiment

Figure 14:
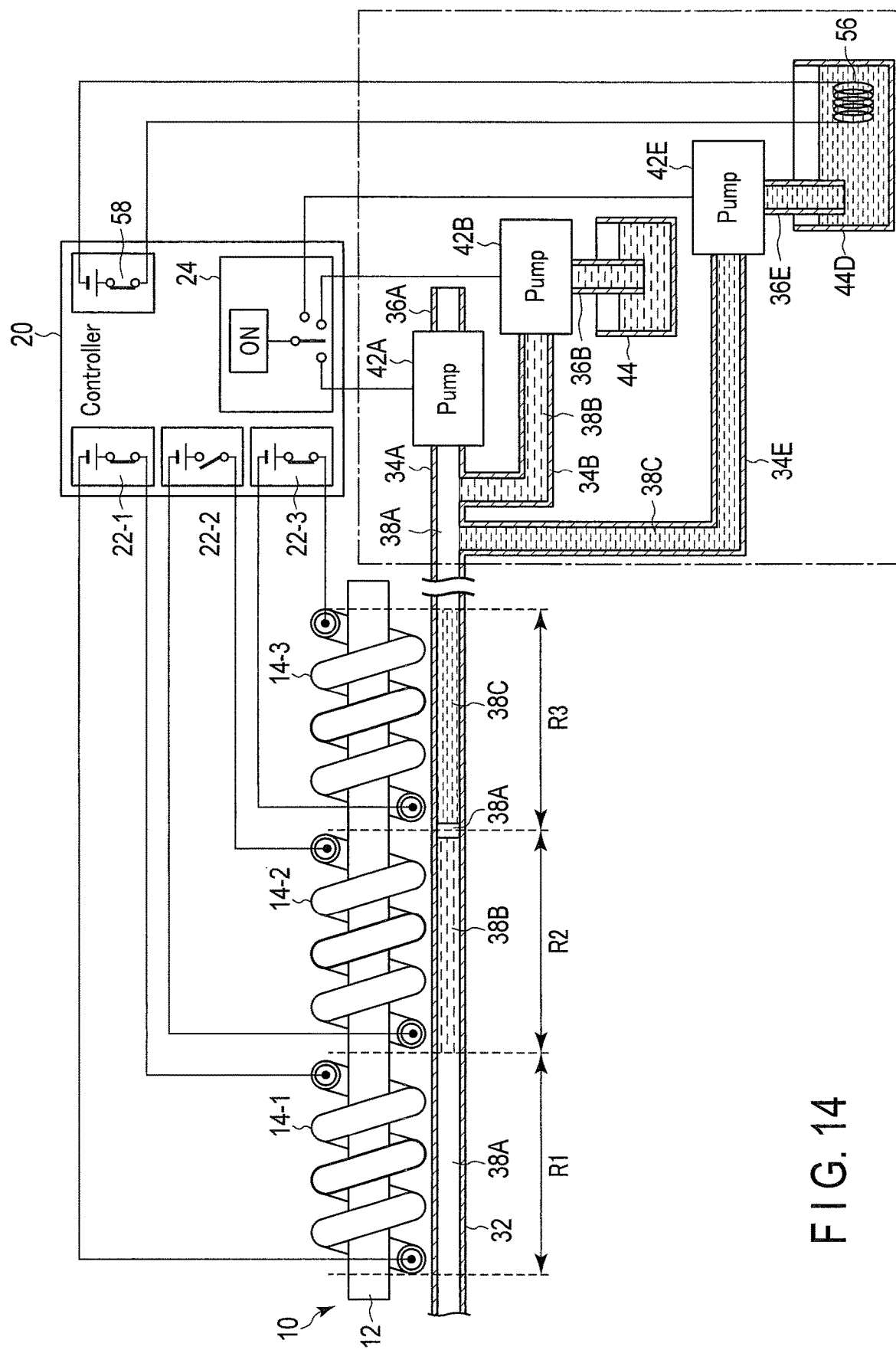
FIG. 14 shows the variable-stiffness actuator system according to the eleventh embodiment.

FIGS. 13 and 14 show a variable-stiffness actuator system according to an eleventh embodiment. In FIGS. 13 and 14, members denoted by the same reference numerals as those shown in FIGS. 1 and 2 are similar members, and a detailed description thereof will be omitted. Hereinafter, the description will focus on different portions. That is, portions not mentioned in the following description are the same as those in the first embodiment.

The variable-stiffness actuator system of the present embodiment is configured such that a pump 42E configured to discharge a heat transmission fluid 38C different from both the heat transmission fluids 38A and 38B is added to the variable-stiffness actuator system of the first embodiment. That is, in addition to the function of discharging the heat transmission fluids 38A and 38B into the channel 32, the transfer section 40 has a function of discharging the heat transmission fluid 38C into the channel 32.

In addition, the variable-stiffness actuator 10 includes an inducing member 14-3 in addition to the inducing members 14-1 and 14-2. The controller 20 includes a driver 22-3 configured to independently drive the inducing member 14-3. Both ends of the inducing member 14-3 are electrically connected to the driver 22-3. Similarly to the drivers 22-1 and 22-2, the driver 22-3 includes a power source and a switch.

The pump 42E is for transferring the heat transmission fluid 38C. The pump 42E has a function of suctioning the heat transmission fluid 38C from a suction port, and discharging the heat transmission fluid 38C from a discharge port. The suction port of the pump 42E is connected to a water intake pipe 36E, and the water intake pipe 36E extends into a tank 44D for storing warm water. A discharge port of the pump 42E is connected to the channel 32 through a connection channel 34E.

Among the heat transmission fluids 38A, 38B, and 38C, at least any one of heat conductivity, heat capacity, viscosity, density, and temperature is different. For example, the heat transmission fluid 38A is air, the heat transmission fluid 38B is room temperature water, and the heat transmission fluid 38C is warm water.

The transfer section 40 also includes a heating wire 56 for warming the water stored in the tank 44D or for keeping warm water warm. In addition, the controller 20 includes a heating wire driver 58 configured to supply a current to the heating wire 56.

FIG. 13 shows a state in which the inducing members 14-1 and 14-2 are driven and the ranges R1 and R2 are heated, but the driving of the inducing member 14-3 is stopped and the range R3 is not heated. FIG. 14 shows a state in which the inducing member 14-1 is driven as it is from the state of FIG. 13 but the driving of the inducing member 14-2 is stopped, and conversely, the inducing member 14-3 is driven. In this state, in the range R1 corresponding to the inducing member 14-1, it is preferable that the heat quantity of the variable-stiffness actuator 10 is not deprived. In the range R2 corresponding to the inducing member 14-2, it is preferable that the heat quantity of the variable-stiffness actuator 10 is deprived quickly. Conversely, in the range R3 corresponding to the inducing member 14-3, it is preferable that the heat quantity of the variable-stiffness actuator 10 is stored quickly. In other words, it is preferable that the portion of the shape-memory member 12 within the range R1 is kept warm, the portion of the shape-memory member 12 within the range R2 radiates heat, and the portion of the shape-memory member 12 within the range R3 is heated.

Accordingly, the pump driver 24 selectively drives the pump 42B for a predetermined time and then stops the pump 42B according to the on/off switching operations of the drivers 22-2 and 22-3. The predetermined time described herein is a time for water as the heat transmission fluid 38B having a volume that fills the internal space of the channel 32 within the range R2 corresponding to the inducing member 14-2 to be transferred into the channel 32 by the pump 42B.

Here, it is assumed that the channel 32 extends to a connection portion of each of the connection channels 34A, 34B, and 34E.

Next, the pump driver 24 selectively drives the pump 42A for a predetermined time, and then stops the pump 42A. The predetermined time described herein is a time for air as the heat transmission fluid 38A having a volume required for water as the heat transmission fluid 38B to be transferred a bit farther forward than the connection channel 34E to be transferred into the channel 32 by the pump 42A.

Subsequently, the pump driver 24 selectively drives a pump 42E for a predetermined time, and then stops the pump 42E. The predetermined time described herein is a time for warm water as the heat transmission fluid 38C having a volume that fills the internal space of the channel 32 within the range R3 corresponding to the inducing member 14-3 to be transferred into the channel 32 by the pump 42E.

As a result, the heat transmission fluids 38B and 38C are present in the internal space of the channel 32 in a state in which they are separated along the channel 32 with the heat transmission fluid 38A therebetween. Since the heat transmission fluid 38A having a low heat conductivity is interposed between the heat transmission fluids 38B and 38C, mixing of the heat transmission fluid 38B, which is water, and the heat transmission fluid 38C, which is warm water, is well prevented, and the movement of heat between the heat transmission fluid 38B and the heat transmission fluid 38C is also well prevented.

Thereafter, the pump driver 24 selectively drives the pump 42A for a predetermined time, and then stops the pump 42A. The predetermined time described herein is a time for air as the heat transmission fluid 38A having a volume required for water as the heat transmission fluid 38B and warm water as the heat transmission fluid 38C previously transferred into the channel 32 to be transferred to the range R2 corresponding to the inducing member 14-2 and the range R3 corresponding to the inducing member 14-3, respectively, to be transferred into the channel 32 by the pump 42A. Thus, the heat transmission fluids 38B and 38C are transferred through the internal space of the channel 32 while a state in which they are separated along the channel 32 with the heat transmission fluid 38A therebetween is maintained.

As a result, the air as the heat transmission fluid 38A is retained in the internal space of the channel 32 within the range R1, the water as the heat transmission fluid 38B is retained in the internal space of the channel 32 within the range R2, and the warm water as the heat transmission fluid 38C is retained in the internal space of the channel 32 within the range R3.

Thus, the heat quantity is well kept in the portion of the shape-memory member 12 within the range R1, the heat radiation of the portion of the shape-memory member 12 within the range R2 is promoted, and the heating of the portion of the shape-memory member 12 within the range R3 is promoted. Thereby, it is achieved to shorten the transition time from the high-stiffness state to the low-stiffness state of the portion of the variable-stiffness actuator 10 within the range R2, and shorten the transition time from the low-stiffness state to the high-stiffness state of the portion of the variable-stiffness actuator 10 within the range R3.

Although an example in which the three kinds of heat transmission fluids 38A, 38B, and 38C are used has been described, the present invention is not limited thereto, and modifications and changes to configurations in which more kinds of heat transmission fluids are used.

The present invention is not limited to the above embodiments themselves. When the invention is reduced to practice, its structural elements can be modified and embodied without departing from the spirit of the invention. Furthermore, a variety of inventions can be made by appropriate combinations of the structural elements of the above embodiments.

What is claimed is:

1. A variable-stiffness actuator system comprising:
   a shape-memory member in which a stiffness increases by being heated and decreases by radiating heat;
   an electric resistance heater arranged along a longitudinal axis direction of the shape-memory member, the electric resistance heater being configured to generate heat in response to supply of a current to heat the shape-memory member;
   a channel arranged along the longitudinal axis direction of the shape-memory member;
   one or more pumps configured to selectively supply a first heat transmission fluid and a second heat transmission fluid different from the first heat transmission fluid into the channel, and stop the supply of the first heat transmission fluid and the second heat transmission fluid into the channel; and a controller comprising hardware, the controller being configured to control the one or more pumps to supply the first heat transmission fluid into the channel and stop the supply of the first heat transmission fluid and supply the second heat transmission fluid into the channel, and further to stop the supply of the second heat transmission fluid into the channel so that retention of the first heat transmission fluid and retention of the second heat transmission fluid simultaneously occur in the channel.

2. The variable-stiffness actuator system according to claim 1, wherein at least one of a first heat conductivity and a first heat capacity of the first heat transmission fluid is different than a second heat conductivity and a second heat capacity of the second heat transmission fluid.

3. The variable-stiffness actuator system according to claim 1, wherein at least one of a first viscosity and a first density of the first heat transmission fluid is different than a second viscosity and a second density of the second heat transmission fluid.

4. The variable-stiffness actuator system according to claim 1, wherein a first temperature of the first heat transmission fluid is different than a second temperature of the second heat transmission fluid.

5. The variable-stiffness actuator system according to claim 1, wherein the first heat transmission fluid and the second heat transmission fluid include at least any one of a solid, liquid, gas, and semisolid.

6. The variable-stiffness actuator system according to claim 1, wherein a first heat conductivity of the first heat transmission fluid is larger than a second heat conductivity of the second heat transmission fluid, or a first heat capacity of the first heat transmission fluid is larger than a second heat capacity of the second heat transmission fluid, and wherein the one or more pumps are configured to retain the first heat transmission fluid in a first range of the channel, and retain the second heat transmission fluid in a second range of the channel, the first range being different from the second range.

7. The variable-stiffness actuator system according to claim 1, wherein the controller controls the one or more pumps based on a control of the electric resistance heater.

8. The variable-stiffness actuator system according to claim 1, further comprising a heat transmission material configured to promote a heat transmission between the channel and the shape-memory member.

9. The variable-stiffness actuator system according to claim 8, wherein the heat transmission material includes a plurality of heat transmission members.

10. The variable-stiffness actuator system according to claim 1, wherein the channel is arranged in parallel to the shape-memory member.

11. The variable-stiffness actuator system according to claim 1, wherein the channel surrounds the electric resistance heater and spirally extends in the longitudinal axis direction.

12. The variable-stiffness actuator system according to claim 1, wherein the channel includes a first channel portion and a second channel portion, the first heat transmission fluid and the second heat transmission fluid flowing in a first direction in the first channel portion and the first heat transmission fluid and the second heat transmission fluid flowing in a second direction, different from the first direction, in the second channel portion.

13. The variable-stiffness actuator system according to claim 1, wherein the one or more pumps are configured to discharge the first heat transmission fluid and the second heat transmission fluid into the channel.

14. The variable-stiffness actuator system according to claim 1, wherein the one or more pumps are configured to suction the first heat transmission fluid and the second heat transmission fluid from the channel.

15. The variable-stiffness actuator system according to claim 1, wherein the one or more pumps are configured to discharge the first heat transmission fluid and the second heat transmission fluid out of a flexible member containing the shape-memory member.

16. The variable-stiffness actuator system according to claim 1, further comprising a storage container configured to store the first heat transmission fluid and the second heat transmission fluid.

17. The variable-stiffness actuator system according to claim 16, wherein the storage container is provided at first end of the channel, the first end being opposite to a second end of the channel to which the one or more pumps are connected.

18. The variable-stiffness actuator system according to claim 1, wherein the channel is formed in the shape-memory member.

19. The variable-stiffness actuator system according to claim 18, wherein the electric resistance heater is arranged in a cavity of the shape-memory member, and the first heat transmission fluid and the second heat transmission fluid comprises an insulator.

20. The variable-stiffness actuator system according to claim 1, wherein a flexible member containing the shape-memory member is an insertion section of an endoscope.

21. A variable-stiffness actuator system comprising:

a shape-memory member in which a stiffness increases by being heated and decreases by radiating heat;

an electric resistance heater arranged along a longitudinal axis direction of the shape-memory member, the electric resistance heater being configured to generate heat in response to supply of a current to heat the shape-memory member;

a channel arranged along the longitudinal axis direction of the shape-memory member;

one or more pumps configured to selectively supply a first heat transmission fluid and a second heat transmission fluid different from the first heat transmission fluid into the channel, and stop the supply of the first heat transmission fluid and the second heat transmission fluid into the channel; and a controller comprising hardware, the controller being configured to cause the one or more pumps to supply the first heat transmission fluid and the second heat transmission fluid into the channel and stop the supply of the first heat transmission fluid and the second heat transmission fluid into the channel so that retention of the first heat transmission fluid and retention of the second heat transmission fluid simultaneously occur in the channel.

* * * * *